US007982873B2

(12) United States Patent
Klassen

(10) Patent No.: US 7,982,873 B2
(45) Date of Patent: Jul. 19, 2011

(54) METHOD AND SYSTEM FOR CORRECTING SPECTROPHOTOMETER DIFFERENCES

(75) Inventor: R. Victor Klassen, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 347 days.

(21) Appl. No.: 12/127,405

(22) Filed: May 27, 2008

(65) Prior Publication Data

US 2009/0296074 A1  Dec. 3, 2009

(51) Int. Cl.
*G01J 3/00* (2006.01)
(52) U.S. Cl. ........... 356/319; 356/72; 702/104; 358/504
(58) Field of Classification Search .................. 356/319; 358/504
See application file for complete search history.

(56) References Cited

U.S. PATENT DOCUMENTS 6,384,918 B1   5/2002   Hubble, III et al.
7,069,164 B2   6/2006   Viturro et al.

OTHER PUBLICATIONS

Mohammadi et al., "Diagnosing and Correcting Systematic Errors in Spectral-Based Digital Imaging," 13th Color Imaging Conference Final Program and Proceedings (Scottsdale, AZ), Society for Imaging Science and Technology & Society for Information Display, pp. 25-30, (Nov. 2005).
Rich et al., "Improved model for improving inter-instrument agreement of spectrocolorimeters," *Analytical Chemica Acta*, 380, 263-276, (1999).
Rich, "Graphical technology—Improving the inter-instrument agreement of spectrocolorimeters," Committee for Graphic Arts Technologies Standard White Paper, pp. 1-27, Reston, Virginia (Jan. 2004).
Berns et al., "Empirical Modeling of Systematic Spectrophotometric Errors," *Color Research and Application*, vol. 13, No. 4, pp. 243-258, (Aug. 1988).

*Primary Examiner* — F. L Evans
(74) *Attorney, Agent, or Firm* — Fay Sharpe LLP

(57) ABSTRACT

A method and system are provided to correct differences among multiple spectrophotometers. In one form, one spectrophotometer of a plurality that may be present in an image rendering system is treated as "primary". Additional spectrophotometers are treated as "secondary". The spectrum of a color from a secondary spectrophotometer is transformed by a linear transformation to an adjusted spectrum, which then is converted to L*a*b* (if desired) using standard techniques. The L*a*b* thus produced is, on average, substantially closer to the L*a*b* that the primary spectrophotometer would have produced when measuring the same color than it is to the L*a*b* that the secondary spectrophotometer would have produced without any correction. The linear transformation is generated by linear regression to minimize the spectral error, followed by non-linear optimization to minimize the error relative to a color difference metric—such as DeltaE 2000.

24 Claims, 3 Drawing Sheets

METHOD AND SYSTEM FOR CORRECTING SPECTROPHOTOMETER DIFFERENCES

BACKGROUND

The use of in-line spectrophotometers in printing systems is increasing. Depending upon the mode of operation, a spectrophotometer will report L*a*b* values, spectral reflectance values at some sampling frequency, and other measurements, such as density. For example, a spectrophotometer typically provides spectral information comprising a representative signal of the printed colors of the image and preferably also provides L*, a*, b* values, XYZ, etc. values depending on the desired color description. One such spectrophotometer may be that disclosed in U.S. Pat. No. 6,384,918 by Hubble, III et al. for a SPECTROPHOTOMETER FOR COLOR PRINTER COLOR CONTROL WITH DISPLACEMENT INSENSITIVE OPTICS, the disclosure of which is hereby incorporated by reference. The spectrophotometer is for non-contact measurement of colored target areas such as test patches on moving printed test sheets in an output path of a color printer, where test patches may be sequentially angularly illuminated with multiple different colors, and a photosensor providing electrical signals in response. The spectrophotometer includes a lens system for transmitting that reflected illumination (multiple illumination sources comprise approximately eight or more individual LEDs) from the test patch. The exemplary spectrophotometer provides non-contact color measurements of moving color targets variably displaced therefrom within normal paper-path baffle spacings.

Customers expect that absolute color accuracy will be improved through the use of these devices, although several factors will conspire to reduce accuracy. These features include cycle-up to cycle-up variability (change in the printer's response between calibration and use); page-to-page variability, and instrument error. Instrument error can be further divided into consistent error and random variation. Random variation cannot be avoided, but can be reduced by averaging. But, instrument error can be reduced by calibrating the spectrophotometer, in particular as described in connection with the presently described embodiments of this application.

It is well known that spectrophotometers have instrument-to-instrument differences, resulting in different responses between instruments reading the same patches printed on the same prints. The solution in the past has been to use a single instrument whenever making comparisons, and to use a single device to measure prints from both engines in a multi-engine color system. A limitation this presents is in a shop or system with multiple engines, each equipped with their own in-line spectrophotometer, the intra-instrument variability is one limiting factor for engine to engine match, unless pages are manually carried to a single instrument. There is, therefore, a need for improved methods of reducing the inter-instrument difference between spectrophotometers.

In this regard, a paper by Roy Berns (R. S. Berns and K. H. Petersen, "Empirical Modeling of Systematic Spectrophotometric Errors", *Color Research and Application,* 13, (4), 243, (1988), which is incorporated herein in its entirety by reference) describes a method of making spectrophotometers match better (in spectral space); another paper by Danny Rich (D. Rich and D. Martin, "Improved model for improving inter-instrument agreement of spectrocolorimeters", *Analytical Chemica Acta,* 380, 263-276, (1999), which is incorporated herein in its entirety by reference, describes an improvement on that method. This method is quoted and used in yet another paper by Rich (D. Rich *Graphic technology—Improving the inter-instrument agreement of spectrocolorimeters* Committee for Graphic Arts Technologies Standards White Paper, Reston, Va. January 2004), which is incorporated herein in its entirety by reference and describes using the method to improve the match of a set of spectrophotometers. The match was generally improved from a mean of 0.447 to 0.191; $75^{th}$ percentile 0.290 to 0.090 and a maximum (over 420 samples) of 1.32 to 1.190.

The model used in both Rich articles is as follows:

$$R_o(\lambda) = \beta_0 + \beta_1 \cdot R_t(\lambda) + \beta_2 \cdot \frac{dR_t(\lambda)}{d\lambda} + \beta_3 \cdot \frac{d^2 R_t(\lambda)}{d\lambda^2}$$

The four beta values are separately optimized for each wavelength. The first represents an offset, the second a scale, the third a linear difference in wavelength scale (referring to a linear error in position of the wavelength samples), and the fourth a bandwidth correction.

Mohammadi and Berns, Diagnosing and Correcting Systematic Errors in Spectral-Based Digital Imaging, $13^{th}$ Color Imaging Conference Final Program and Proceedings (Scottsdale, Ariz.), Society for Imaging Science and Technology & Society for Information Display (November 2005), which is incorporated herein in its entirety by reference, went further, adding quadratic terms for both scale and wavelength scale, and a sinusoidal wavelength scale term. The quadratic and sinusoidal wavelength scale were least frequently significant in the regressions (one regression per wavelength).

In all of these methods, three point numerical first and second derivative formulas are used, which means that the adjustments to the input reflectances are entirely dependent on the reflectances themselves, and the two adjacent reflectances.

BRIEF DESCRIPTION

In one aspect of the presently described embodiments, the method comprises computing a correction for reflectance values at selected wavelengths, the correction comprising a series of coefficients multiplied by correction terms, and summed to obtain a summed result, and, applying the correction to select spectrophotometers by converting the summed result to a selected color space.

In another aspect of the presently described embodiments, the method further comprises measuring first reflectance values of a test pattern by a first spectrophotometer to obtain output values and measuring second reflectance values of test pattern by a second spectrophotometer to obtain the correction terms.

In another aspect of the presently described embodiments, the computing comprises performing a linear regression on the output values and the correction terms to obtain the coefficients.

In another aspect of the presently described embodiments, the coefficients are significant coefficients for each selected wavelength.

In another aspect of the presently described embodiments, the computing comprises performing a non-linear optimization.

In another aspect of the presently described embodiments, the non-linear optimization comprises a conjugate gradient minimization.

In another aspect of the presently described embodiments, the method further comprises performing a second non-linear optimization.

In another aspect of the presently described embodiments, the selected color space is XYZ.

In another aspect of the presently described embodiments, the selected color space is L*a*b*.

In another aspect of the presently described embodiments, the method further comprises calibrating one of the print engines.

In another aspect of the presently described embodiments, the system comprises a first spectrophotometer operative to measure first reflectance values of a test pattern to obtain output values, a second spectrophotometer operative to measure second reflectance values of test pattern to obtain correction terms and a controller operative to compute a correction for reflectance values at selected wavelengths, the correction comprising a series of coefficients multiplied by correction terms, and summed to obtain a summed result and apply the correction to select spectrophotometers by converting the summed result to a selected color space.

In another aspect of the presently described embodiments, the controller is operative to perform a linear regression on the output values and the correction terms to obtain the coefficients.

In another aspect of the presently described embodiments, the coefficients are significant coefficients for each selected wavelength.

In another aspect of the presently described embodiments, the controller is operative to perform a non-linear optimization.

In another aspect of the presently described embodiments, the non-linear optimization comprises a conjugate gradient minimization.

In another aspect of the presently described embodiments, the controller is operative to perform a second non-linear optimization.

In another aspect of the presently described embodiments, the selected color space is XYZ.

In another aspect of the presently described embodiments, the selected color space is L*a*b*.

In another aspect of the presently described embodiments, the controller is operative to calibrate at least one of the print engines.

In another aspect of the presently described embodiments, the system comprises a first spectrophotometer operative to measure first reflectance values of a test pattern to obtain output values, a second spectrophotometer operative to measure second reflectance values of test pattern to obtain correction terms, and, a controller operative to compute a correction for reflectance values at selected wavelengths, the correction comprising a series of coefficients multiplied by correction terms, and summed to obtain a summed result, and apply the correction to select spectrophotometers by converting the summed result to a selected color space, wherein the correction terms are obtained using a non-linear optimization.

In another aspect of the presently described embodiments, initial estimates of the correction terms are obtained using linear regression.

In another aspect of the presently described embodiments, the non-linear optimization uses an objective function defined using a color difference metric.

In another aspect of the presently described embodiments, least significant correction terms are dropped.

In another aspect of the presently described embodiments, the correction terms include well-spaced wavelengths.

DETAILED DESCRIPTION

According to the presently described embodiments, the problem of differences in spectrophotometer performance is addressed. In one form, one spectrophotometer of a plurality that may be present in an image rendering system is treated as "primary". Additional spectrophotometers are treated as "secondary". The spectrum of a color from a secondary spectrophotometer is transformed by a linear transformation to an adjusted spectrum, which then is converted to L*a*b* (if desired) using standard techniques. The L*a*b* thus produced is, on average, substantially closer to the L*a*b* that the primary spectrophotometer would have produced when measuring the same color than it is to the L*a*b* that the secondary spectrophotometer would have produced without any correction. The linear transformation is generated by linear regression to minimize the spectral error, followed by non-linear optimization to minimize the error relative to a color difference metric such as DeltaE 2000.

The presently described embodiments provide an advantageous result because, when using a spectrophotometer to measure a printed patch on a page, it is less important that the reflectances be correct than that the result, when converted to L*a*b* with an appropriate illuminant, be as close to correct as possible. This leads to a somewhat different approach to improving spectrophotometer performance than those approaches noted above and used thus far.

In this regard, if the paper and toner are known, the error (or inter-instrument difference) can be characterized in terms of a few dominant wavelengths. One might expect the instrument to have an error in one direction for reddish colors, and perhaps a different error for bluish colors. If the correction does depend on the input color, then factors influencing the error term would include a sampling of reflectances sufficiently far apart to give an estimate of the hue and saturation.

Figure 1:
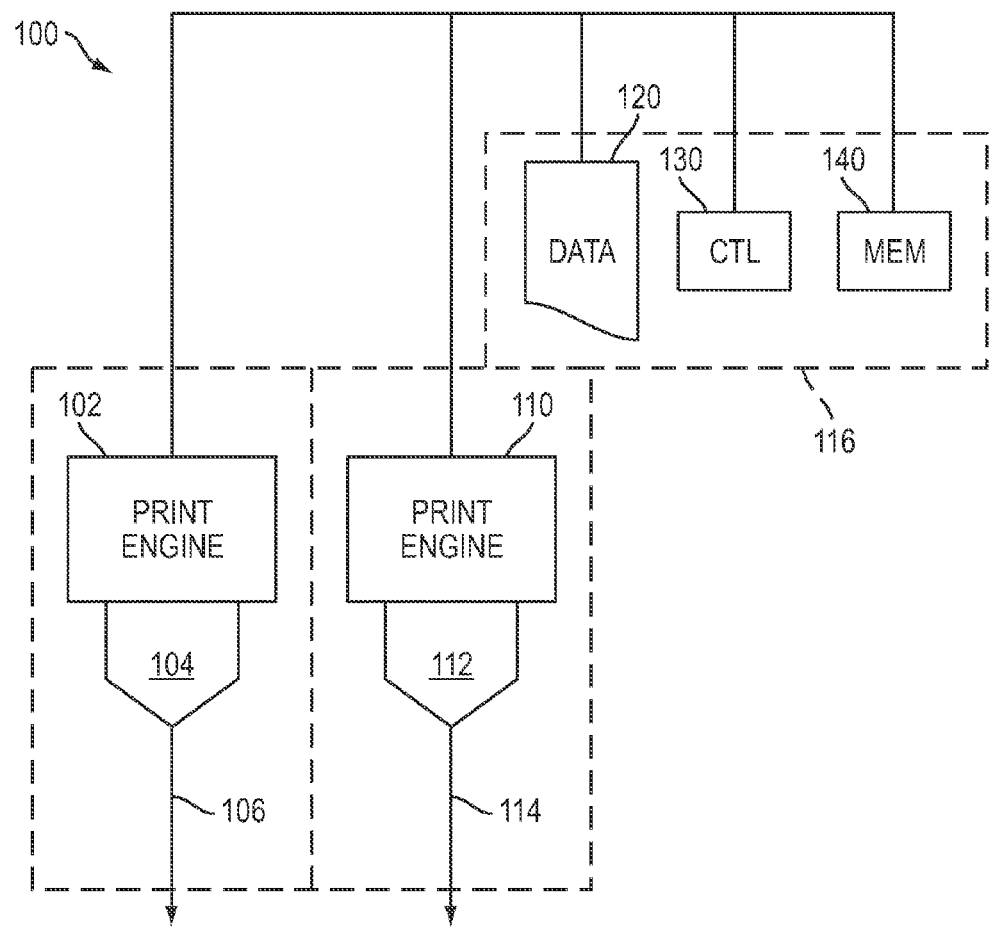
FIG. 1 is a block diagram of a system into which the presently described embodiments may be implemented.

With reference now to FIG. 1, an image rendering or printing system 100 into which the presently described embodiments may be incorporated is shown. The system 100 includes a first print engine 102 having a first color sensing device such as spectrophotometer 104 associated therewith. It should be understood that the color sensing device or spectrophotometer is generally positioned in an in-line fashion at the output of the print engine 102 along an output path 106, and may take a variety of forms (including those noted above).

A second print engine 110 having a second color sensing device such as spectrophotometer 112 is also illustrated. The spectrophotometer 112 is provided in an in-line fashion along output path 114 of the print engine 110. The system 100 is also provided with a system manager 116 that includes a data or input source or file 120, a controller 130, and a memory 140.

In operation, the system manager 116 controls the rendering of images by the print engine 102 and/or the print engine 110. In this regard, data is provided from data source 120, which may take a variety of forms, including that of a print job file.

It should be appreciated that the image rendering system 100 may be implemented in a variety of configurations and may also include many elements that are not shown. Illustrated elements are included in this description for the purpose of explaining the presently described embodiments. Further, the print engine 102 and the print engine 110 may be under common control of a system manager, such as system manager 116, or may be separately controlled by dedicated system managers. Likewise, the print engines 102 and 110 are shown as having separate output paths 106 and 114. However, the print engines may share an output path. Also, for ease of illustration, two print engines having in-line spectrophotometers are shown. However, it is contemplated that the presently described embodiments may be applied in any system having a plurality of print engines with (in-line or off-line) spectrophotometers. An example of a system with multiple off-line spectrophotometers is a multiple-shop print provider where each shop has its own spectrophotometer, and the multiple spectrophotometers need to match each other, even though they may be across the globe from each other. In addition, such embodiments may be applied in any system having a need of multiple spectrophotometers, with a need to match the responses of the spectrophotometers.

Further, the system 100 may be implemented in a multitude of ways including as a single printer having multiple print engines, or modular components serving as print engines. Alternatively, the system 100 may comprise a plurality of stand-alone printers or print engines under common control. Or, the system 100 may comprise a plurality of stand-alone systems that are linked for the purpose of calibration and the like.

Figure 2:
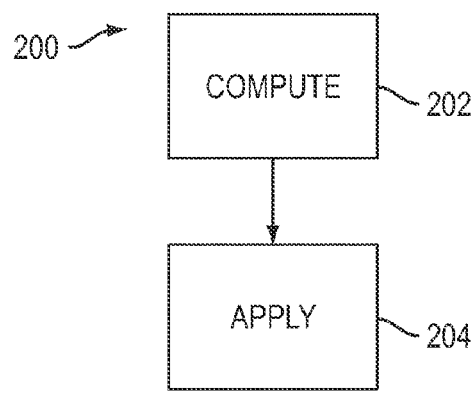
FIG. 2 is a flow chart illustrating a method according to the presently described embodiments.

With reference to FIG. 2, there are two primary aspects to a method 200: computing a correction (at 202) and applying the computed correction (at 204). One form of the computing will also be described in connection with FIG. 3. Likewise, an example of the applying is described in connection with FIG. 4.

It should be understood that the method 200 (and the associated exemplary methods 300, and 400, and others according to the presently described embodiments) may be implemented using a variety of hardware configurations and/or software techniques. For example, routines embodying these methods and stored in the memory 140 (FIG. 1) may be executed by the controller 130 (FIG. 1) to calibrate the spectrophotometers 104 and 112 (FIG. 1). In this way, image data stored in data source 120 may be processed and rendered in an improved manner. Of course, other implementations may suffice as well.

Referring back now to FIG. 2, the computing of the correction (at 202) comprises, for each wavelength, a determining of a series of coefficients, which are multiplied by the following correction terms, and summed:

$R_0$, $R_1$, $R_2$, the reflectances at the wavelength in question, and two others at spacings of 100 nm from it.
$R_0 R_1$, $R_0 R_2$, $R_1 R_2$ and $R_0^2$
$dR/d\lambda$, $d^2R/d\lambda^2$
1 (for a constant offset).

Note that as commonly practiced, printers having four inks (cyan, magenta, yellow and black (CMYK)), the printers are calibrated for many purposes using combinations of not more than three inks (CMY being used for achieving grey balance). For this reason three representative reflectances $R_0$, $R_1$ and $R_2$ are adequate. For a printer having more inks, and where it is calibrated using more than three inks at a time, a larger number of wavelengths (and hence representative reflectances) may be required. In at least one form of the presently described embodiments, the representative reflectances are selected at well-spaced wavelengths. In a spectral space sampled from 400 nm to 700 nm, 100 nm spacing works well for three well-spaced wavelengths. For four well-spaced wavelengths, 75 nm spacing works well.

The determination is, in one form, performed using linear regression, which yields as its output not only the coefficients but their level of statistical significance. The significant coefficients provide an estimate for the correction terms.

Insignificant coefficients can either be set to zero, (and then multiplied by their corresponding terms) or marked as insignificant and then not included in the sum.

A non-linear optimization (to be described in greater detail below) is also used to obtain an advantageous result for the correction.

Applying the correction (at 204) includes using the computed sum (as above at 202) and then converting to XYZ using a selected white point and the tabulated standard observer XYZ and finally converting to L*a*b* using the standard formula.

The applying of the correction (at 204) includes the $R_0$, $R_1$, $R_2$, quadratic and interaction terms in the list of correction terms.

Figure 3:
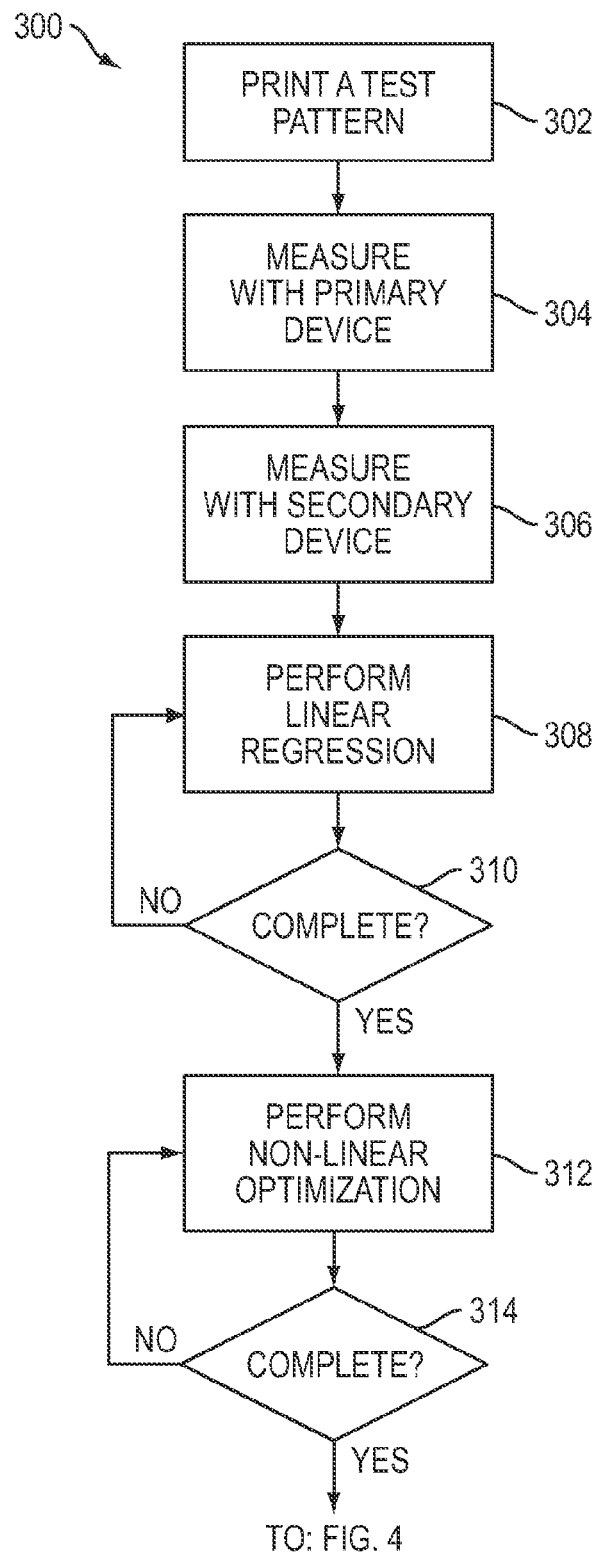
FIG. 3 is a flow chart illustrating a method according to the presently described embodiments.

With reference now to FIG. 3, in one form, the computing of the correction is accomplished using a method 300. Initially, a page or pages containing, preferably, a representative sampling of color space is printed (at 302), and measured on the primary (at 304) and secondary instruments (at 306). The printing may be accomplished on any of the subject print engines, or others.

For each wavelength, for each measured patch, the measurement of the secondary instrument is used to compute the correction terms. The measurement of that wavelength on the primary instrument is used as the desired output for that patch. The correction terms and output values are used in linear regression (at 308) to determine a vector of correction coefficients, that when multiplied with a vector of correction terms gives the output—i.e., the vector that produces an output which, in a least squares sense is minimally different from the desired output, over all patches. After a set of coefficients is found, they are tested for significance, and one or more of the least significant terms is dropped, and the solution is re-computed. Once no terms with significance greater than a threshold (preferably $p<0.05$), remain, any insignificant terms are either zeroed or marked as insignificant. In this process, it is continuously determined if the linear regression is complete (at 310).

In one example form, a linear regression was accomplished using terms that include the measured reflectance at the subject wavelength, the measured reflectances of wavelengths at, for example, 100 nm steps away from that one, quadratic and one way interactions between these and a second derivative term. So, this was accomplished for wavelengths 400, 440, 500, 540, 600 and 640 (nm). In practice, three reflectances are usually significant, quadratics and second derivatives are significant half the time, and two way interactions are occasionally significant. $R^2$ values generally exceed 0.998.

After linear regression has been applied to obtain a vector of significant correction coefficients for each wavelength, non-linear optimization is applied to reduce the L*a*b* error (at 312). In at least one form, the significant correction coefficients are treated as initial estimates of the correction terms for the non-linear optimization. In this phase, the objective function is the sum of the squared DeltaE values, comparing the L*a*b* computed from the corrected reflectances with the L*a*b* values reported by the primary instrument. Other objective functions are possible, such as the sum of the DeltaE values, or a weighted sum. The free parameters are all of the significant terms from the linear regression phase. Conjugate gradient minimization or any other well-known non-linear optimization process may be used here.

The choice of DeltaE is arbitrary. One might use any of the several color difference metrics known in the art (or a new one). For example, $\Delta E_{ab}$, $\Delta E_{94}$, $\Delta E2000$ or $\Delta E(CMC)$ may all be used. The advantage of these color difference metrics is that differences between two colors as measured using one of these metrics are more indicative of visual differences than differences between spectra.

A determination is made as to whether the process is complete (at 314). In this regard, one additional non-linear optimization may be implemented to make small adjustments to the spectral distribution of the white point used in converting to XYZ. In at least one advantageous form, adjustments greater than the quantization error in the tabulated values are heavily penalized.

Figure 4:
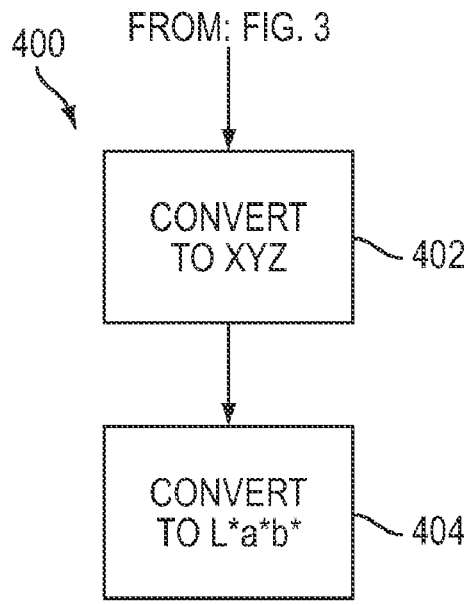
FIG. 4 is a flow chart illustrating a method according to the presently described embodiments.

With reference now to FIG. 4, a method 400 is shown. It should be understood that the method 400 reflects the functionality of the box 204 of FIG. 2. As shown, the method 400 includes a step of converting the reflectance values to XYZ (at 402). Subsequently, the XYZ values are converted to L*a*b* color space (at 404). Of course, conversion of the values to any suitable color space could be accomplished.

The method of FIGS. 2-4 was applied to two DTP-70 instruments (made by the X-Rite Corporation) measuring a page printed on a Xerox DC250 color laser printer. $\Delta E2000$ was used in the objective function, and it is the metric reported below. The page was measured five times on each instrument, and the average used as the value for that instrument. Multiple variants were tried for comparison; results appear in the table below:

TABLE 1

$\Delta E2000$ differences between the corrected values from a secondary instrument and those of the primary instrument

|  | RMS | 80 | 90 | 95 | 99 | max |
|---|---|---|---|---|---|---|
| White point only | 0.248 | 0.293 | 0.347 | 0.431 | 0.623 | 1.150 |
| Linear - bandwidth terms only | 0.514 | 0.544 | 0.735 | 0.938 | 1.532 | 1.617 |
| Linear - additional wavelengths only | 0.510 | 0.558 | 0.712 | 0.955 | 1.485 | 1.577 |
| Linear - bandwidths plus wavelengths | 0.519 | 0.561 | 0.742 | 1.002 | 1.477 | 1.569 |
| Redo white point | 0.188 | 0.196 | 0.254 | 0.315 | 0.551 | 1.407 |
| Optimize spectral terms | 0.134 | 0.168 | 0.205 | 0.242 | 0.306 | 0.427 |
| Redo white point again | 0.135 | 0.169 | 0.206 | 0.247 | 0.309 | 0.423 |
| Joint optimize | 0.134 | 0.167 | 0.202 | 0.244 | 0.305 | 0.432 |

For comparison, a single instrument was used to measure the same page five times (after the page had cooled overnight to be stable). Each of the five measurements was compared to each of the four others, yielding 10 comparisons. The percentiles were taken across patches, and then averaged across measurement pairs, yielding the results below.

TABLE 2

Single instrument repeatability. RMS differences are smaller than inter-instrument; the distribution has a longer tail.

| RMS | 80 | 90 | 95 | 99 | max |
|---|---|---|---|---|---|
| 0.1053 | 0.1175 | 0.1541 | 0.1945 | 0.3192 | 0.5224 |

So, the exemplary embodiments described result in clear advantages. Nonetheless, many variants of the presently described embodiments may be implemented. In one variant, spectra are reduced to principal components coefficients before being further processed. The method could be applied to the principal components coefficients rather than the spectra themselves. Or, it could be applied to the principal components of one device to produce principal components of the other device. Here, the presently described embodiments introduce using L*a*b* difference in a non-linear optimization.

In another variant, the wavelengths used might be the wavelength being corrected, plus the dominant wavelength in the reflectance spectra of each of the colorants being printed (except black). This generalizes nicely to more colorants than CMYK. Alternatively, where more colorants are being used, the spectra could be sampled more finely than every 100 nm.

Figure 5:
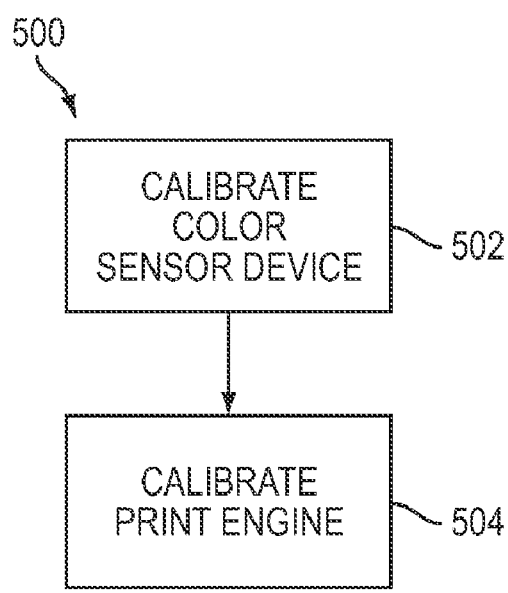
FIG. 5 is a flow chart illustrating a method according to the presently described embodiments.

Once a correction has been made for making a second or secondary, for example, spectrophotometer behave more like the master or primary device, that spectrophotometer may be used to calibrate one or more printers, resulting in a better match between the output of printers calibrated with the second spectrophotometer and printers calibrated with the master device. In this regard, the applying of the correction (e.g. at 204 of FIG. 2) may be used to correct colors measured to calibrate a print engine. So, with reference to FIG. 5, a method 500 is illustrated. In this embodiment, the spectrophotometers or color sensing devices of the system (e.g. spectrophotometers 104 and 112) are calibrated (at 502). Then, a spectrophotometer or color sensing device (e.g. secondary spectrophotometer) is used to calibrate at least one of the printers or print engines (e.g. print engines 102 and 110) (at 504). Of course, the primary spectrophotometer may also be used for the calibration, as those of skill in the art will appreciate.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method for calibrating a plurality of spectrophotometers in a printing system having multiple print engines, the method comprising:
   computing a correction for reflectance values at selected wavelengths, the correction comprising a series of coefficients multiplied by correction terms, and summed to obtain a summed result; and,
   applying the correction to select spectrophotometers by converting the summed result to a selected color space.

2. The method as set forth in claim 1 further comprising measuring first reflectance values of a test pattern by a first spectrophotometer to obtain output values and measuring second reflectance values of the test pattern by a second spectrophotometer to obtain the correction terms.

3. The method as set forth in claim 2 wherein the computing comprises performing a linear regression on the output values and the correction terms to obtain the coefficients.

4. The method as set forth in claim 3 wherein the coefficients are significant coefficients for each selected wavelength.

5. The method as set forth in claim 1 wherein the computing comprises performing a non-linear optimization.

6. The method as set forth in claim 5 wherein the non-linear optimization comprises a conjugate gradient minimization.

7. The method as set forth in claim 5 further comprising performing a second non-linear ptimization.

8. The method as set forth in claim 1 wherein the selected color space is XYZ.

9. The method as set forth in claim wherein the selected color space is L*a*b*.

10. The method as set forth in claim 1, further comprising calibrating one of the print engines.

11. A system for calibrating a plurality of spectrophotometers, each associated with a print engine, the system comprising:
   a first spectrophotometer operative to measure first reflectance values of a test pattern to obtain output values;
   a second spectrophotometer operative to measure second reflectance values of the test pattern to obtain correction terms; and,
   a controller operative to compute a correction for reflectance values at selected wavelengths, the correction comprising a series of coefficients multiplied by correction terms, and summed to obtain a summed result, and to apply the correction to select spectrophotometers by converting the summed result to a selected color space.

12. The system as set forth in claim 11 wherein the controller is operative to perform a linear regression on the output values and the correction terms to obtain the coefficients.

13. The system as set forth in claim 12 wherein the coefficients are significant coefficients for each selected wavelength.

14. The system as set forth in claim 11 wherein the controller is operative to perform a non-linear optimization.

15. The system as set forth in claim 14 wherein the non-linear optimization comprises a conjugate gradient minimization.

16. The system as set forth in claim 14 wherein the controller is operative to perform a second non-linear optimization.

17. The system as set forth in claim 11 wherein the selected color space is XYZ.

18. The system as set forth in claim 11 wherein the selected color space is L*a*b*.

19. The system as set forth in claim 11, wherein the controller is operative to calibrate at least one of the print engines.

20. A system for calibrating a plurality of spectrophotometers, the system comprising:
   a first spectrophotometer operative to measure first reflectance values of a test pattern to obtain output values;
   a second spectrophotometer operative to measure second reflectance values of the test pattern to obtain correction terms; and,
   a controller operative to compute a correction for reflectance values at selected wavelengths, the correction comprising a series of coefficients multiplied by correction terms, and summed to obtain a summed result, and apply the correction to select spectrophotometers by converting the summed result to a selected color space, wherein the correction terms are obtained using a non-linear optimization.

21. The system of claim 20, wherein initial estimates of the correction terms are obtained using linear regression.

22. The system of claim 20, wherein the non-linear optimization uses an objective function defined using a color difference metric.

23. The system of claim 21, wherein least significant correction terms are dropped.

24. The system of claim 20, wherein the correction terms include well-spaced wavelengths.

* * * * *